United States Patent
Park et al.

(10) Patent No.: US 11,959,781 B2
(45) Date of Patent: Apr. 16, 2024

(54) MAT FOR SENSING HUMAN BODY MOVEMENT WITH SENSOR ARRAY

(71) Applicant: LG Electronics Inc., Seoul (KR)

(72) Inventors: Hyungyu Park, Seoul (KR); Seonghyok Kim, Seoul (KR); Suhyang Kim, Seoul (KR); Jeongwook An, Seoul (KR); Younjae Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 908 days.

(21) Appl. No.: 16/936,714

(22) Filed: Jul. 23, 2020

(65) Prior Publication Data

US 2020/0348154 A1 Nov. 5, 2020

Related U.S. Application Data

(63) Continuation of application No. PCT/KR2018/003341, filed on Mar. 22, 2018.

(30) Foreign Application Priority Data

Jan. 23, 2018 (KR) ........................ 10-2018-0008366

(51) Int. Cl.
*G01D 5/26* (2006.01)
*A47C 21/00* (2006.01)
(Continued)

(52) U.S. Cl.
CPC ............. *G01D 5/268* (2013.01); *A47C 21/00* (2013.01); *A61B 5/1116* (2013.01);
(Continued)

(58) Field of Classification Search
None
See application file for complete search history.

(56) References Cited

U.S. PATENT DOCUMENTS

| | | | |
|---|---|---|---|
| 2007/0008156 A1 | 1/2007 | Ueda et al. | |
| 2017/0156662 A1* | 6/2017 | Goodall | A61N 2/002 |
| 2017/0164876 A1* | 6/2017 | Hyde | A61B 5/1118 |

FOREIGN PATENT DOCUMENTS

| | | |
|---|---|---|
| JP | 2006271978 | 10/2006 |
| KR | 20-2009-0009178 | 5/2009 |

(Continued)

OTHER PUBLICATIONS

Office Action in Korean Appln. No. 10-2018-0008366, dated Jun. 20, 2022, 12 pages (with English translation).

*Primary Examiner* — Brandi N Hopkins
*Assistant Examiner* — Nigel H Plumb
(74) *Attorney, Agent, or Firm* — Fish & Richardson P.C.

(57) ABSTRACT

A human body sensing mat can sense the movement of a human body and analyze a user's sleep. The human body sensing mat may include a substrate; a plurality of fiber sensors for generating signals according to a distance to a specific object; a sensor array disposed on the substrate; a shield layer for covering the sensor array; and a driving unit for applying a voltage to the sensor array. Each of the fiber sensors is disposed on a central portion of the substrate and on both ends of the substrate. The fiber sensors that are respectively disposed in the central portion and end portions of the mat can sense the user's breathing, tossing and turning, and the like regardless of the user's posture. Accordingly, the user's sleep can be analyzed regardless of the user's posture.

12 Claims, 7 Drawing Sheets

(51) Int. Cl.
*A61B 5/00* (2006.01)
*A61B 5/11* (2006.01)
*G01P 13/00* (2006.01)
*A61B 5/08* (2006.01)

(52) U.S. Cl.
CPC .......... *A61B 5/4806* (2013.01); *A61B 5/6892* (2013.01); *G01P 13/00* (2013.01); *A61B 5/0816* (2013.01); *A61B 2562/182* (2013.01)

(56) References Cited

FOREIGN PATENT DOCUMENTS

| | | | |
|---|---|---|---|
| KR | 2020090009178 | * | 9/2009 |
| KR | 10-2012-0031847 | | 4/2012 |
| KR | 101147955 | | 5/2012 |
| KR | 10-2015-0057184 | | 5/2015 |
| KR | 20150057184 | * | 5/2015 |
| KR | 20150057429 | | 5/2015 |
| KR | 101730999 | | 4/2017 |
| KR | 20170084883 | | 7/2017 |
| KR | 10-2017-0115121 | | 10/2017 |

* cited by examiner

MAT FOR SENSING HUMAN BODY MOVEMENT WITH SENSOR ARRAY

CROSS-REFERENCE TO RELATED APPLICATIONS

This application is a continuation of International Application No. PCT/KR2018/003341, filed on Mar. 22, 2018, which claims the benefit of earlier filing date and right of priority to Korean Application No. 10-2018-0008366, filed on Jan. 23, 2018, the contents of which are incorporated herein by reference in their entirety.

TECHNICAL FIELD

The present disclosure relates to a human body sensing mat capable of analyzing a user's movement and biological signals.

BACKGROUND

Sleep is important for physical and mental health. Proper sleep can help in reducing fatigue, improving immunity and concentration, relieving stress, reducing inflammation, repairing muscles, and the like.

Accordingly, sleep assistance devices, sleep guidance devices, or sleep analysis devices for assisting in proper and effective sleep have been developed. However, such devices typically use various sensors that need to be worn on a user's body. This may cause inconvenience to the user in getting proper sleep, and the use of the sensors may be cumbersome. Accordingly, there is an increasing demand for a device capable of analyzing the user's movement and biological signals without wearing it on his or her body.

In some examples, as shown in FIG. 1, the user's movement and biological signals may be analyzed by placing a sensor 110 at the bottom of bedding. However, the operation of the sensor 110 may depend highly on the user's sleeping posture, and thus the user's sleep analysis may be difficult when the user sleeps in a specific posture. For example, when the user sleeps in a first posture 10 as shown in FIG. 1, the sensor 110 may accurately analyze sleep. However, when the user sleeps in a second posture 21 as shown in FIG. 2, the sensor 110 may not operate for accurate sleep analysis.

SUMMARY

An aspect of the present disclosure provides a human body sensing mat capable of analyzing a user's movement and biological signals regardless of the user's posture.

Particular implementations of the present disclosure provide a mat that senses an object on the mat. The mat may include a substrate, a sensor array, a shield layer, and a drive unit. The sensor array may be disposed on the substrate and include a plurality of fiber sensors. Each of the plurality of fiber sensors may be configured to generate a signal based on a distance between the object and the fiber sensor. The shield layer may cover the sensor array. The drive unit may be configured to apply a voltage to the sensor array. The plurality of fiber sensors may be disposed at opposite ends of the substrate and between the opposite ends of the substrate.

In some implementations, the mat may optionally include one or more of the following features. The mat may include a plurality of connection electrodes that are disposed at an edge of the substrate and electrically connect the plurality of fiber sensors with the drive unit. The shield layer may cover the plurality of connection electrodes and may be configured to restrict an electromagnetic field. The shield layer may include a portion that is disposed at the edge of the substrate. The drive unit may be configured to output sleep information of the object based on the signal that is generated from each of the plurality of fiber sensors. The signal may correspond to an impedance change that is caused by the distance between the object and the fiber sensor. The drive unit may be configured to calculate posture information of the object based on the signal that is generated from each of the plurality of fiber sensors. The drive unit may be further configured to output the sleep information of the object based on (i) the signal that is generated from each of the plurality of fiber sensors and (ii) the posture information. The drive unit may be configured to weight the signal that is generated from each of the plurality of fiber sensors based on the posture information. The drive unit may be configured to output the sleep information of the object based on the weighted signal.

Particular implementations of the present disclosure provide a method for sensing an object on a mat. The mat may include a substrate, a drive unit, and a sensor array that is disposed on the substrate and that includes a plurality of fiber sensors. The plurality of fiber sensors may be disposed at opposite ends of the substrate and between the opposite ends of the substrate. The method may include applying, using the drive unit, a voltage to the sensor array; receiving, at the drive unit, a signal from each of the plurality of fiber sensors, the signal be representative of a distance between the fiber sensor and the object; and generating, using the drive unit, sleep information of the object based on the signal.

In some implementations, the method may optionally include one or more of the following features. The signal may correspond to an impedance change that is caused by the distance between the fiber sensor and the object. The method may include calculating, using the drive unit, posture information of the object based on the signal that is generated from each of the plurality of fiber sensors. The method may include outputting, using the drive unit, the sleep information of the object based on (i) the signal that is generated from each of the plurality of fiber sensors and (ii) the posture information. The method may include weighting, using the drive unit, the signal that is generated from each of the plurality of fiber sensors based on the posture information. Generating sleep information of the object may include outputting, using the drive unit, the sleep information based on the weighted signal. The mat may include a shield layer that covers the sensor array. The mat may include a plurality of connection electrodes that are disposed at an edge of the substrate and electrically connect the plurality of fiber sensors with the drive unit. The shield layer may cover the plurality of connection electrodes and may be configured to block an electromagnetic field. The shield layer may be disposed at the edge of the substrate.

In order to achieve the above objective and other objectives, implementations of the present disclosure provide a human body sensing mat for sensing the movement of a human body. Particular implementations of the present disclosure provide a human body sensing mat that senses the movement of a human body, including a substrate, a sensor array, a shield layer, and a drive unit. The sensor array may include a plurality of fiber sensors that can generate signals according to a distance from a specific object and that can be disposed on the substrate. The shield layer can cover the sensor array. The drive unit can apply a voltage to the sensor array. Each of the fiber sensors can be disposed at a central portion of the substrate and both ends of the substrate, respectively.

Implementations of the present disclosure may further include a plurality of connection electrodes arranged at an edge of the substrate to electrically connect each of the fiber sensors and the drive unit.

Implementations of the present disclosure may further include a shield layer that covers the connection electrodes and blocks an electromagnetic field.

The shield layer may be formed at an edge of the substrate.

The drive unit may output a user's sleep information using a signal generated from each of the fiber sensors.

The signal may be an impedance change caused by a distance between the user and each of the fiber sensors.

The drive unit may calculate the user's posture information based on a signal generated from each of the fiber sensors, and output the sleep information using the signal generated from each of the fiber sensors and the posture information.

The drive unit may weight a signal generated from each of the fiber sensors based on the posture information, and output the sleep information using the weighted signal.

According to implementations of the present disclosure, fiber sensors may be arranged at a distal end portion and a central portion of a mat, respectively, and therefore can sense a user's breathing, tossing and turning, and the like, regardless of the user's posture on the mat. With these configurations, the mat according to implementations of the present disclosure may analyze the user's movement and biological signals regardless of the user's posture.

In addition, according to implementations of the present disclosure, different signals may be generated according to the position of a mat, and therefore may be used to recognize the user's sleeping posture. The present disclosure may improve the accuracy of sleep analysis using the user's sleeping posture information.

DETAILED DESCRIPTION

Figure 1:
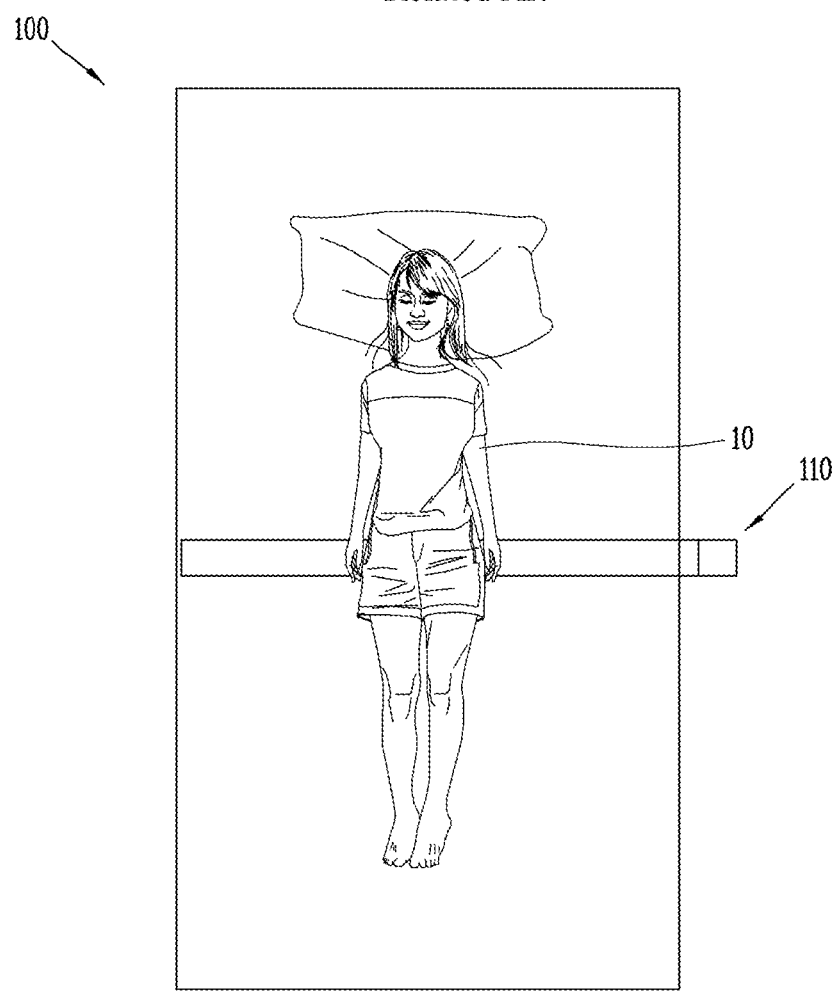
FIGS. 1 and 2 illustrate a human body sensing mat in the related art of the present disclosure.
Figure 2:
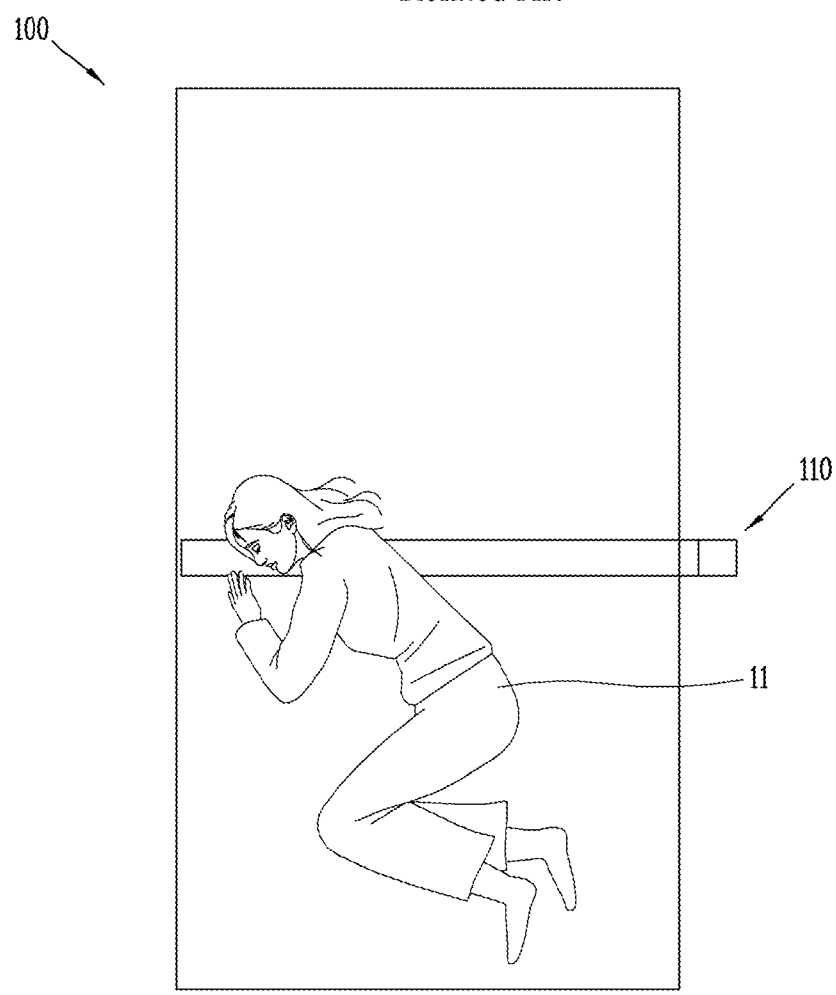

Hereinafter, implementations of the present disclosure will be described in detail with reference to the accompanying drawings, and the same or similar elements are designated with the same numeral references in the drawings. Description of known elements or processes will be omitted. It should be understood that the accompanying drawings are merely illustrative, and therefore, they should not be construed to limit the present disclosure. The present disclosure should be construed as being extended to all modifications, equivalents, and substitutes included in the concept and technological scope of the present disclosure.

Hereinafter, a human body sensing mat according to implementations of the present disclosure will be described with reference to the accompanying drawings. Although examples of analyzing a user's sleep using a human body sensing mat are primarily described herein, the human body sensing mat according to implementations of the present disclosure may not be limited to analysis of the user's sleep, but may be similarly used to analyze other aspects, such as user's movement and biological signals.

Figure 3:
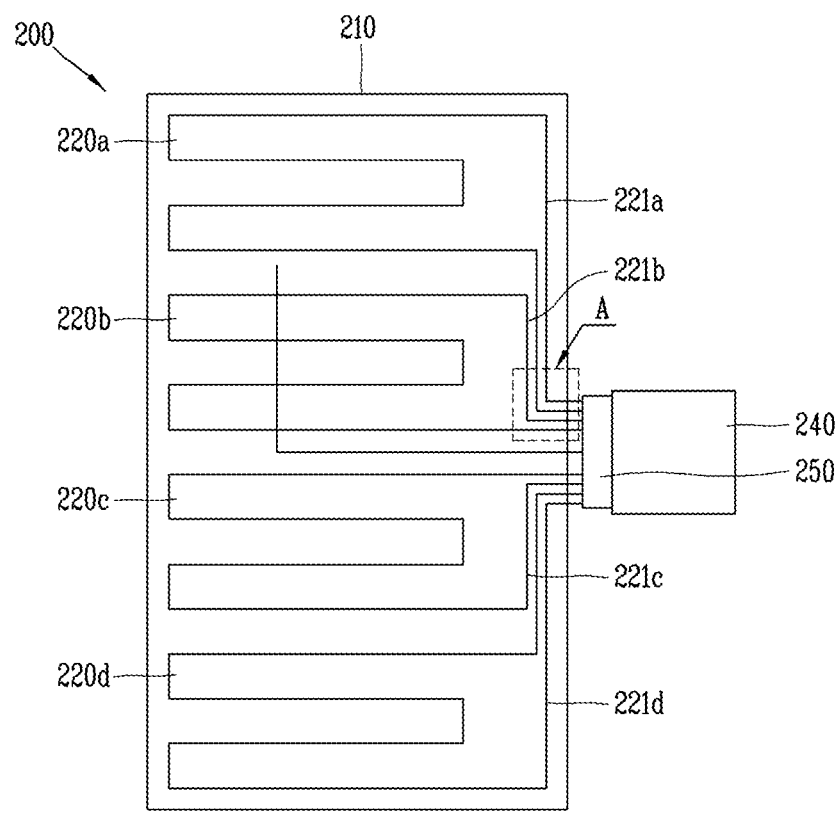
FIG. 3 is a schematic view of an example human body sensing mat according to implementations of the present disclosure.
Figure 4:
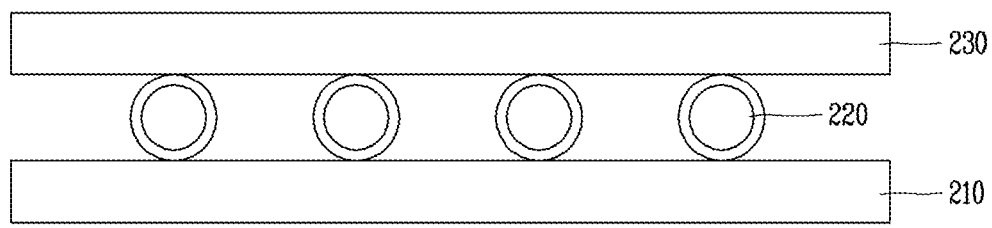
FIG. 4 is a cross-sectional view of an example human body sensing mat according to implementations of the present disclosure.

Referring to FIG. 3, a human body sensing mat 200 according to implementations of the present disclosure may include a substrate 210, sensor arrays 220a to 220d, a shield layer 230, and a drive unit 240. The human body sensing mat may include more or less components than those described herein.

The substrate 210 is configured to fix the sensor arrays 220a to 220d and the shield layer 230. In some implementations, the substrate 210 may be preferably made of a bendable, flexible material so that the mat can be used in various states, such as a fully unfolded state or a partially folded state.

The material of the substrate 210 may include, but not limited to, a bendable and washable material due to the characteristics of the mat.

The sensor arrays 220a to 220d can be arranged on the substrate 210. The sensor arrays 220a to 220d can include a plurality of fiber sensors 220a to 220d that can generate signals according to their distances from a specific object. In some implementations, each of the fiber sensors 220a to 220d may be formed of an electrode, and an impedance value of the electrode can change according to a distance between the electrode and a specific object.

For example, each of the fiber sensors 220a to 220d may include an LC tank circuit. The LC tank circuit may include a sensor that infers a change in capacitance from an oscillation frequency amount that is shifted according to the capacitance change. When using the LC tank circuit, it may be possible to sense a distance between a user's body and one or more of the fiber sensors.

In some implementations, an impedance change in each of the fiber sensors 220a to 220d may be measured and used to calculate the user's posture and breathing pattern.

Figure 5:
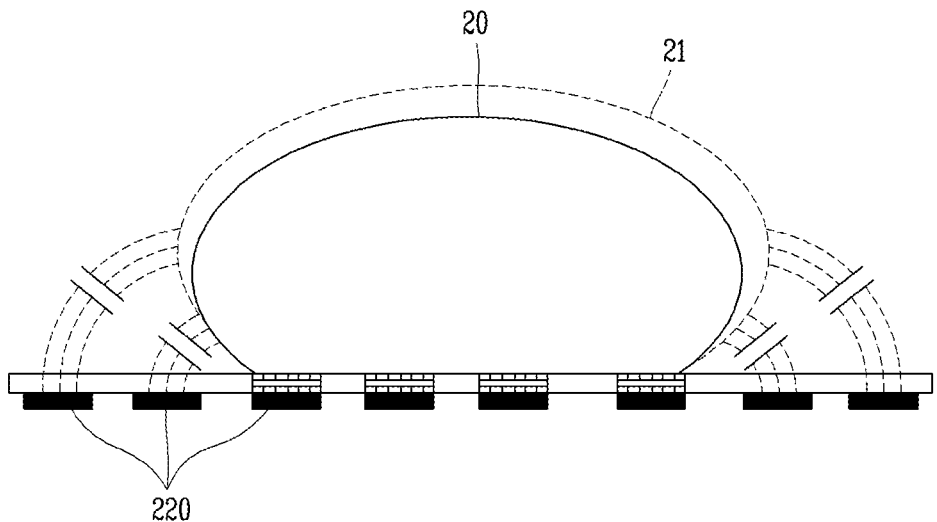
FIG. 5 illustrates a principle of an LC-tank.

For example, as shown in FIG. 5, an impedance value of the fiber sensor 220 when the user is lying on a mat in a first state 20 can be different from an impedance value of the fiber sensor 220 when the user is in a second state 21 through breathing. The drive unit 240 may sense a change in the impedance value of the fiber sensor 220 to analyze the user's breathing pattern.

An impedance change of the fiber sensors 220 may be caused by a distance change between the user and the fiber sensors, even though the fiber sensors are not in contact with the user's body. Therefore, using the fiber sensors, the user's sleep may be analyzed without making the sensors contact the user.

The fiber sensors 220a to 220d may be respectively arranged at a central portion of the substrate and at opposite ends of the substrate. In some implementations, as shown in FIG. 3, the fiber sensors 220a to 220d may be arranged side by side in a longitudinal direction of the mat.

Since different signals may be generated from the fiber sensors, respectively, at least one of the fiber sensors may sense the user's posture and breathing pattern, regardless of where the user is located on the mat.

In some implementations, each of the fiber sensors 220 may be formed of a stranded or Litz structure. With these configurations, it may be possible to increase sensing sensitivity, compared to a single-line structure.

Figure 6:
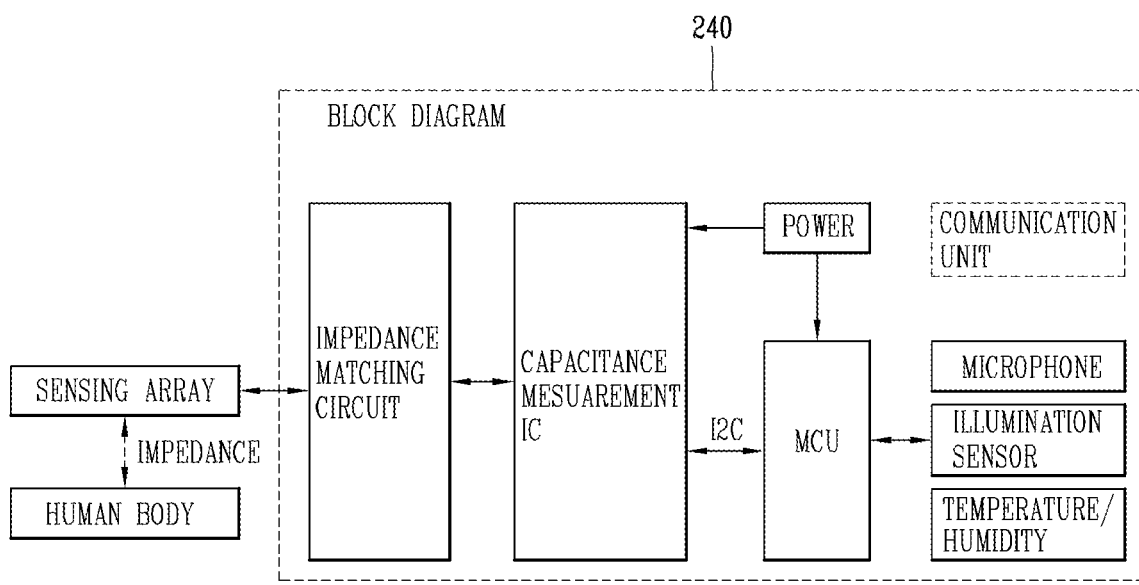
FIG. 6 illustrates an example drive unit according to implementations of the present disclosure.

In some implementations, in order to cause an impedance change of the fiber sensors 220, a voltage may be applied to the fiber sensors. The drive unit 240 may apply a voltage to each of the fiber sensors 220a to 220d, and measures an impedance change of each of the fiber sensors 220a to 220d. For example, as shown in FIG. 6, the drive unit 240 may include an impedance matching circuit, a capacitance measurement circuit, a power supply unit, and an MCU. The drive unit 240 may further include a communication unit for wireless communication with an external terminal.

In some implementations, the drive unit 240 may be configured to be detachable from the mat 200. For example, implementations of the present disclosure may further include a connection portion 250 that can be electrically connected to the connection electrodes 221a to 221d. The connection portion 250 may be configured to be detachable from the drive unit 240. The user may easily connect the drive unit 240 to the connection electrodes 221a to 221d by coupling the drive unit 240 to the connection portion 250. The user may remove the drive unit 240 and then wash only the remaining portion, thereby facilitating the washing of the mat.

In some implementations, the human body sensing mat may include at least one of a temperature sensor, a humidity sensor, an illuminance sensor, or an acoustic sensor. The drive unit 240 may provide information related to sleep based on information sensed by the sensors.

For example, the drive unit 240 may collectively analyze the ambient temperature, humidity, illuminance, and/or noise level of the mat, and output a sleep environment level (e.g., score) to the user. The more suitable these elements are for the sleeping environment or condition, the higher the level (e.g., score) may be output. The user may check the sleep condition level (e.g., score) and act to increase the sleep condition level. For example, when ambient humidity is low and thus the sleep condition level is low, the user may operate a humidifier or the like to increase the ambient humidity, thereby increasing the sleep condition level.

In some implementations, the mat 200 may further include connection electrodes 221a to 221d that can electrically connect the drive unit 240 with the fiber sensors 220a to 220d. For example, the connection electrodes 221a to 221d may be arranged at an edge of the substrate to electrically connect each of the fiber sensors 220a to 220d with the drive unit 240. Since a separate connection electrode is connected to each of the fiber sensors 220a to 220d, there may be a plurality of connection electrodes.

The plurality of connection electrodes may overlap with or come close to each other at a specific point on the substrate. For example, as shown in a region "A" of FIG. 3, the number of overlapping or adjacent connection electrodes increases as they approach the drive unit.

The connection electrodes 221a to 221d may be made of the same material as the fiber sensors. In this case, the connection electrodes 221a to 221d may generate signals according to their distances from a specific object. In some implementations, the signals generated from the connection electrodes 221a to 221d may be difficult to distinguish from the signals generated from the fiber sensors 220a to 220d connected to the connection electrodes, and therefore the connection electrodes may be regarded as part of the sensors.

The connection electrodes may be used as part of the sensors without a problem at a position where the connection electrodes 221a to 221d do not overlap or are disposed closely with each other. However, using the connection electrodes as part of the sensors may cause a problem at a position where the plurality of connection electrodes overlap or are disposed closely with each other.

For example, when signals that are generated from the connection electrodes 221a to 221d arranged adjacent to the drive unit 240 and overlapped (or disposed closely) with each other as shown in a region "A" of FIG. 3, are used for sleep analysis, it is difficult to determine whether a signal are generated from the fiber sensor 220a located at a distal end portion of the substrate or generated from the fiber sensor 220b located at a central portion of the substrate. Therefore, when the user comes close to or comes into contact with a position adjacent to the drive unit 240 during sleep, an inaccurate sleep analysis may result.

In order to prevent such problems, the mat according to implementations of the present disclosure may further include a shield portion that covers the connection electrodes 221a to 221d and shields an electromagnetic field.

Figure 7:
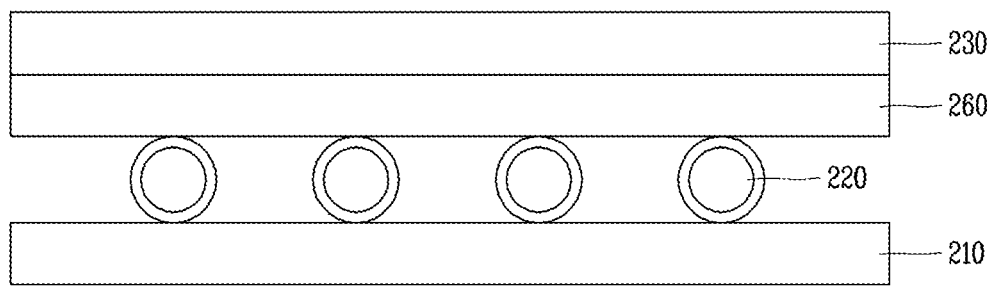
FIGS. 7 and 8 are cross-sectional views of example mats that include example shield portions.
Figure 8:
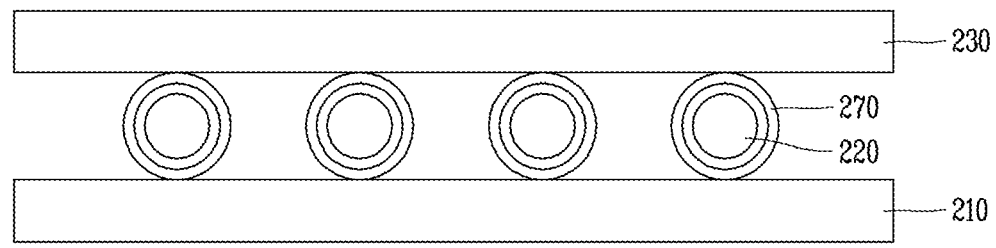

FIGS. 7 and 8 are cross-sectional views of example mats provided with a shield portion.

The shield portion may block an electromagnetic field to prevent occurrence of an impedance change of the connection electrode according to a distance change between the connection electrode and a specific object. When the shield portion is disposed at an edge of the substrate that includes the connection electrode, it may be possible to reduce or prevent occurrence of an impedance change in the connection electrode. With these configurations, it may be possible to reduce or prevent generation of an incorrect signal at a position where the connection electrodes overlap with each other. In some implementations, as shown in FIG. 7, the shield portion 260 may be made in a sheet shape. In other implementations, as shown in FIG. 8, the shield portion 270 may be made in a shape surrounding the connecting electrode.

As described above, the shield portion can allow accurate sleep analysis even when the user approaches a region where the connection electrodes overlap with (or are disposed closely) each other during sleep.

Figure 9:
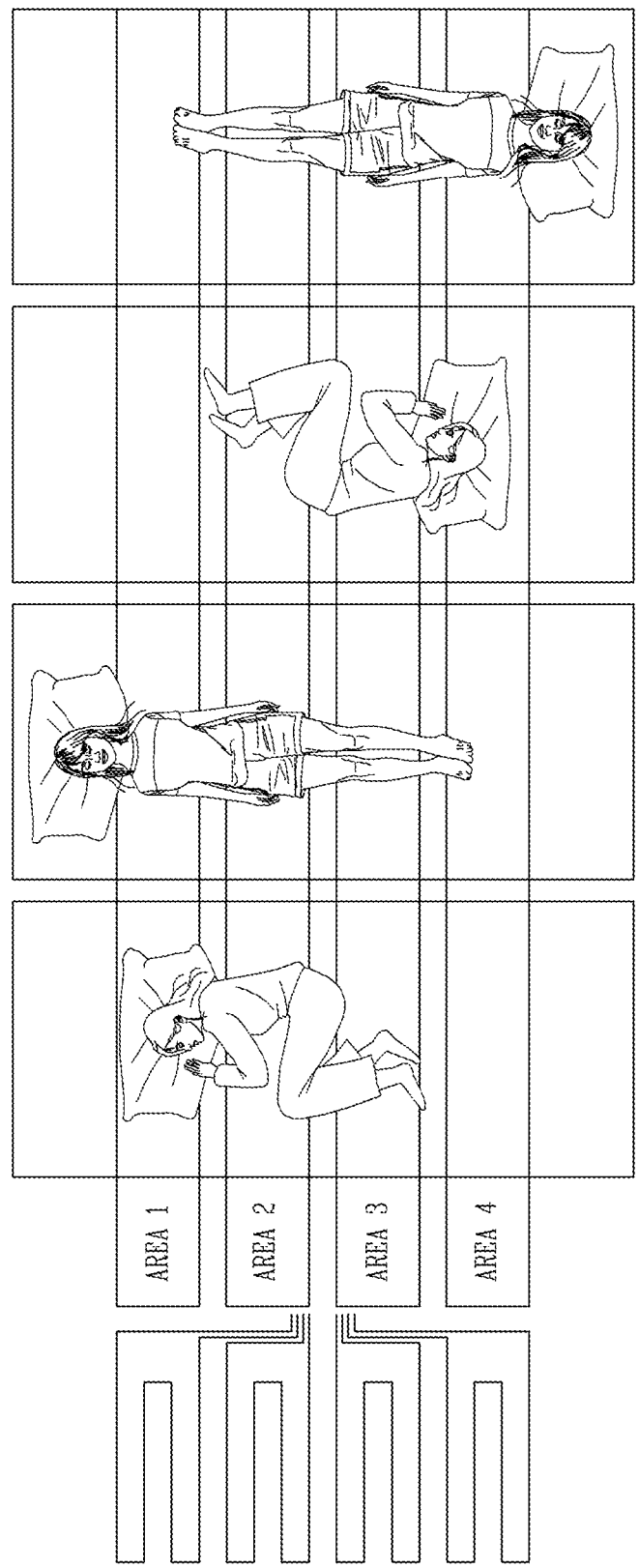
FIG. 9 illustrates example use of the human body sensing mat according to implementations of the present disclosure.

Hereinafter, an example application of the human body sensing mat according to implementations of the present disclosure will be described. In some implementations, as shown in FIG. 9, the fiber sensors are arranged in four areas such that, regardless of the user's sleep posture, a signal may be generated in at least one of the four areas to identify the user's posture change or breathing pattern. With these configurations, the present disclosure may analyze the user's sleep regardless of the user's sleeping posture.

Figure 10:
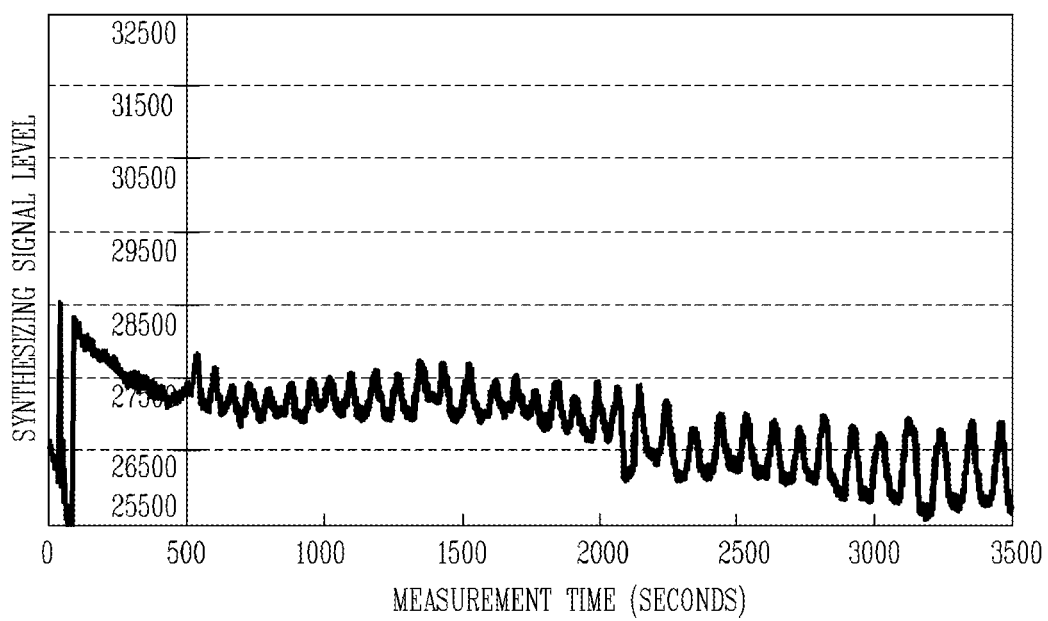
FIG. 10 is a graph of an example result of synthesizing the signals that are generated from the fiber sensors.

FIG. 10 is a graph showing an example result of synthesizing the signals generated from the fiber sensors.

The x-axis in FIG. 10 represents a measurement time (seconds). A signal between 0 to 500 seconds shows that the user has sleep apnea. A signal between 500 to 2000 seconds shows that the user has normal breath. A signal between 2000 to 3500 seconds shows that the user has sleep breathing. As shown in the graph of FIG. 10, it may be seen that the user's sleep apnea, normal breathing and sleep breathing are clearly distinguished.

In some implementations, according to the present disclosure, the signals that are generated from the fiber sensors arranged at each position of the mat may be synthesized to improve the accuracy of sleep analysis. Hereinafter, an example control method of a drive unit for improving accuracy of a user's sleep analysis using the human body sensing mat will be described.

The drive unit 240 may calculate user's posture information based on a signal generated from each of the fiber sensors, and may output sleep information based on the signal generated from each of the fiber sensors and the posture information.

For example, the drive unit 240 may calculate a region of the mat that is occupied by the user using the fiber sensors. As shown in FIG. 9, when the user is in a first posture that occupies only Areas 1 to 3, a signal is generated only from the fiber sensors arranged in Areas 1 to 3. Based on this, the drive unit 240 may determine that the user is sleeping in a crouched posture. When the user is in a second posture that occupies all of Areas 1 to 4, signals are generated from all of the fiber sensors arranged in Areas 1 to 4. Based on this, the drive unit 240 may determine that the user is sleeping while straightening the body.

In some implementations, the drive unit 240 may output the sleep information to an output unit that is separately provided on the mat or a terminal that is capable of wireless communication with the drive unit 240.

In some implementations, the drive unit 240 may weight a signal that is generated from each of the fiber sensors based on the calculated posture information, and may output the sleep information based on the weighted signal.

For example, in analyzing the user's breathing pattern, the drive unit 240 may give a higher weight to a signal generated from a fiber sensor disposed in a specific area than signals from other fiber sensors. For example, the drive unit 240 may predict an area where the user's chest portion is located from the posture information, and give the highest weight to a signal generated from a fiber sensor disposed in the area where the chest portion is located. This is because the body part where the most changes occur when the user breathes is the chest portion.

For example, when the user is sleeping like the first posture illustrated in FIG. 9, the drive unit 240 may predict that the user's chest portion is disposed in Area 2 from the posture information, and give the highest weight to a signal generated from the fiber sensor disposed in Area 2 to analyze the user's breathing pattern.

As described above, the user's sleep can be analyzed based on the user's posture, thereby improving the accuracy of sleep analysis.

It is understood to those skilled in the art that the present disclosure can be embodied in other specific forms without departing from the concept and essential characteristics thereof. Furthermore, the detailed description of the present disclosure should not be construed as restrictive in all aspects but considered as illustrative. The scope of the invention should be determined by reasonable interpretation of the appended claims and all changes that come within the equivalent scope of the invention are included in the scope of the invention.

What is claimed is:

1. A mat that senses an object on the mat, the mat comprising:
a substrate;
a sensor array that is disposed on the substrate and that includes a plurality of fiber sensors, each of the plurality of fiber sensors configured to generate a signal based on a distance between the object and the fiber sensor;
a shield layer that covers the sensor array;
a drive unit configured to apply a voltage to the sensor array;
a plurality of connection electrodes that are disposed at an edge of the substrate and electrically connect the plurality of fiber sensors with the drive unit; and
a shield portion disposed at the edge of the substrate, the shield portion having a shape that surrounds the plurality of connection electrodes and being configured to block an electromagnetic field to thereby restrict an impedance change of the plurality of connection electrodes based on a distance change between the plurality of connection electrodes and the object,
wherein the plurality of fiber sensors are disposed at opposite ends of the substrate and at a central portion between the opposite ends of the substrate.

2. The mat of claim 1, wherein the drive unit is configured to:
sense a change in impedance value of the plurality of fiber sensors, the impedance value including (i) a first impedance value based on a user lying on a mat in a first state and (ii) a second impedance value based on the user being in a second state through breathing; and
output sleep information by calculating a posture and a breathing pattern of the user based on the change in impedance value sensed by each of the plurality of fiber sensors.

3. The mat of claim 2, wherein the drive unit is configured to calculate posture information of the object based on the signal that is generated from each of the plurality of fiber sensors.

4. The mat of claim 3, wherein the drive unit is further configured to output the sleep information of the object based on (i) the signal that is generated from each of the plurality of fiber sensors and (ii) the posture information.

5. The mat of claim 3, wherein the drive unit is configured to weight the signal that is generated from each of the plurality of fiber sensors based on the posture information.

6. The mat of claim 5, wherein the drive unit is configured to output the sleep information of the object based on the weighted signal.

7. A method for sensing an object on a mat, wherein the mat comprises:
a substrate;
a drive unit;
a sensor array that is disposed on the substrate and that includes a plurality of fiber sensors, wherein the plurality of fiber sensors is disposed at opposite ends of the substrate and between the opposite ends of the substrate;
a plurality of connection electrodes that are disposed at an edge of the substrate and electrically connect the plurality of fiber sensors with the drive unit; and
a shield portion disposed at the edge of the substrate, the shield portion having a shape that surrounds the plurality of connection electrodes,
the method comprising:
applying, using the drive unit, a voltage to the sensor array;
receiving, at the drive unit, a signal from each of the plurality of fiber sensors, the signal be representative of a distance between the fiber sensor and the object, wherein the shield portion is configured block an electromagnetic field to thereby restrict an impedance change of the plurality of connection electrodes based on a distance change between the plurality of connection electrodes and the object; and generating, using the drive unit, sleep information of the object based on the signal.

8. The method of claim 7, wherein the signal corresponds to an impedance change that is caused by the distance between the fiber sensor and the object.

9. The method of claim 7, further comprising:
sensing a change in impedance value of the plurality of fiber sensors, the impedance value including (i) a first impedance value based on a user lying on a mat in a first state and (ii) a second impedance value based on the user being in a second state through breathing; and
calculating, using the drive unit, posture information and a breathing pattern of the user based on the signal that is generated from each of the plurality of fiber sensors.

10. The method of claim 9, further comprising:
outputting, using the drive unit, the sleep information of the object based on (i) the signal that is generated from each of the plurality of fiber sensors and (ii) the posture information.

11. The method of claim 9, further comprising:
weighting, using the drive unit, the signal that is generated from each of the plurality of fiber sensors based on the posture information.

12. The method of claim 11, wherein generating sleep information of the object comprises:
outputting, using the drive unit, the sleep information based on the weighted signal.

* * * * *